United States Patent [19]

Sladek

[11] Patent Number: 4,951,661
[45] Date of Patent: Aug. 28, 1990

[54] QUICK-CONNECT ADAPTER VALVE FOR CONNECTING NEBULIZER AND FLUID VENTILATOR HOSE

[75] Inventor: David T. Sladek, Tucson, Ariz.

[73] Assignee: Thayer Medical Corporation, Tucson, Ariz.

[21] Appl. No.: 387,401

[22] Filed: Jul. 31, 1989

Related U.S. Application Data

[63] Continuation of Ser. No. 204,014, Jun. 8, 1988, abandoned.

[51] Int. Cl.$^5$ .............................................. A62B 9/04
[52] U.S. Cl. ........................... 128/202.27; 128/205.24; 128/912
[58] Field of Search ................... 128/911, 912, 200.14, 128/202.27, 203.12, 204.25, 205.24; 137/563

[56] References Cited

U.S. PATENT DOCUMENTS

| | | | |
|---|---|---|---|
| 2,820,651 | 1/1958 | Phillips | 285/151 |
| 3,724,489 | 4/1973 | Eross | 137/322 |
| 3,731,717 | 5/1973 | Potash | 141/379 |
| 3,806,086 | 4/1974 | Cloyd | 251/149.7 |
| 4,276,876 | 7/0781 | Häkkinen | 128/205.24 |
| 4,281,652 | 8/1981 | Miller | 128/911 |
| 4,351,327 | 9/1982 | Rinne et al. | 128/200.14 |
| 4,385,629 | 5/1983 | Wolf, Jr. et al. | 128/912 |
| 4,446,863 | 5/1984 | Rubin et al. | 128/204.18 |
| 4,506,665 | 3/1985 | Andrews et al. | 128/202.27 |
| 4,508,117 | 4/1985 | Rodari | 128/204.25 |
| 4,596,246 | 6/1986 | Lyall | 128/202.27 |
| 4,612,929 | 9/1986 | Schübert et al. | 128/912 |
| 4,637,384 | 1/1987 | Schroeder | 128/204.18 |
| 4,657,047 | 4/1987 | Kolibas | 137/563 |
| 4,846,167 | 7/1989 | Tibbals | 128/912 |

Primary Examiner—Edgar S. Burr
Assistant Examiner—Aaron J. Lewis
Attorney, Agent, or Firm—Cahill, Sutton & Thomas

[57] ABSTRACT

A disposable adapter valve inserted into a T connector in a ventilator hose allows connecting and disconnecting a nebulizer to the hose without loss of positive and expiratory pressure (PEEP). An integral press-on cap covers the open end of the adapter valve when the nebulizer or a drain container is not connected, preventing leakage of fluids and preventing contamination of the inner surface of the adapter valve by airborne bacteria and the like.

5 Claims, 2 Drawing Sheets

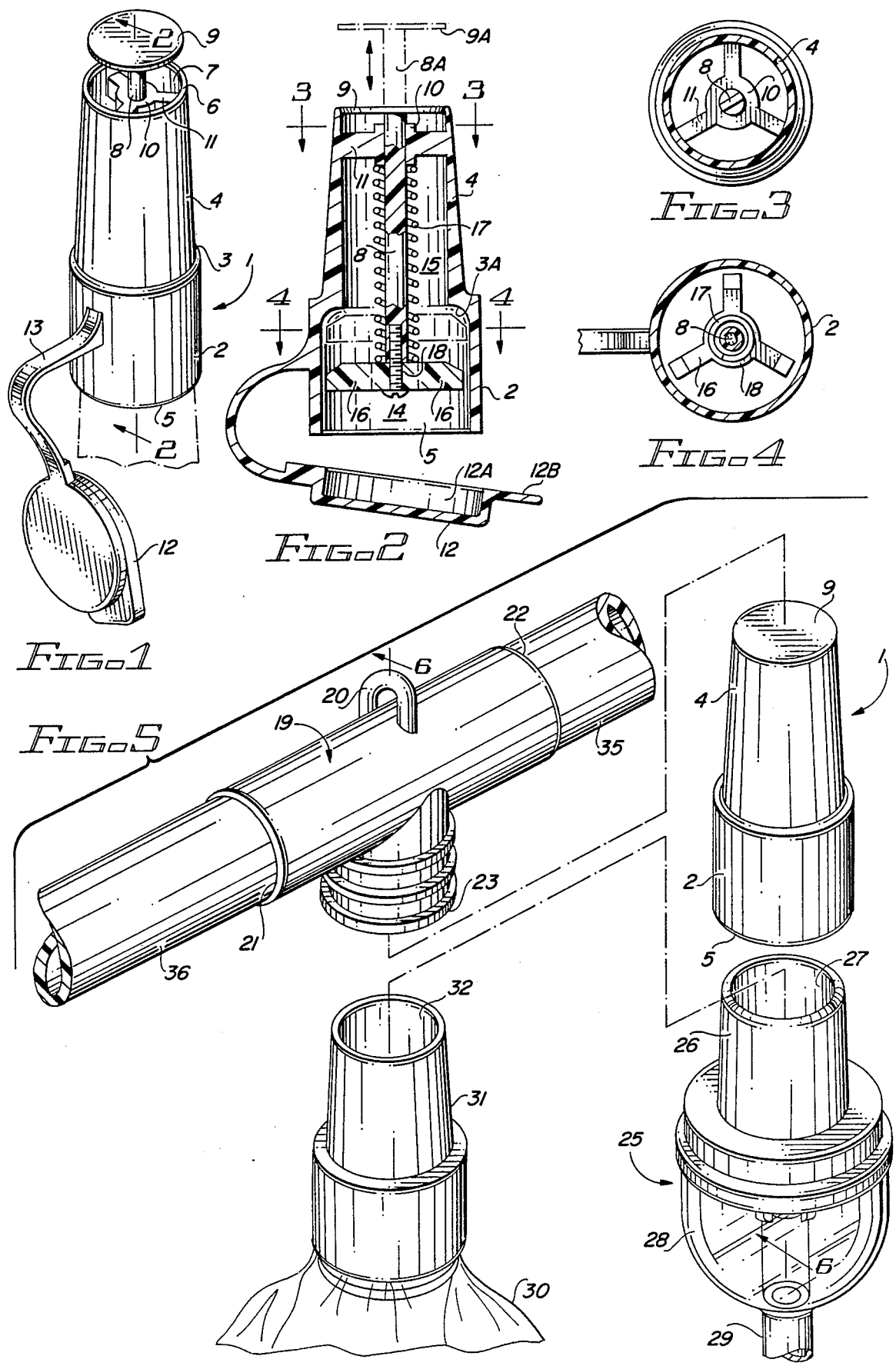

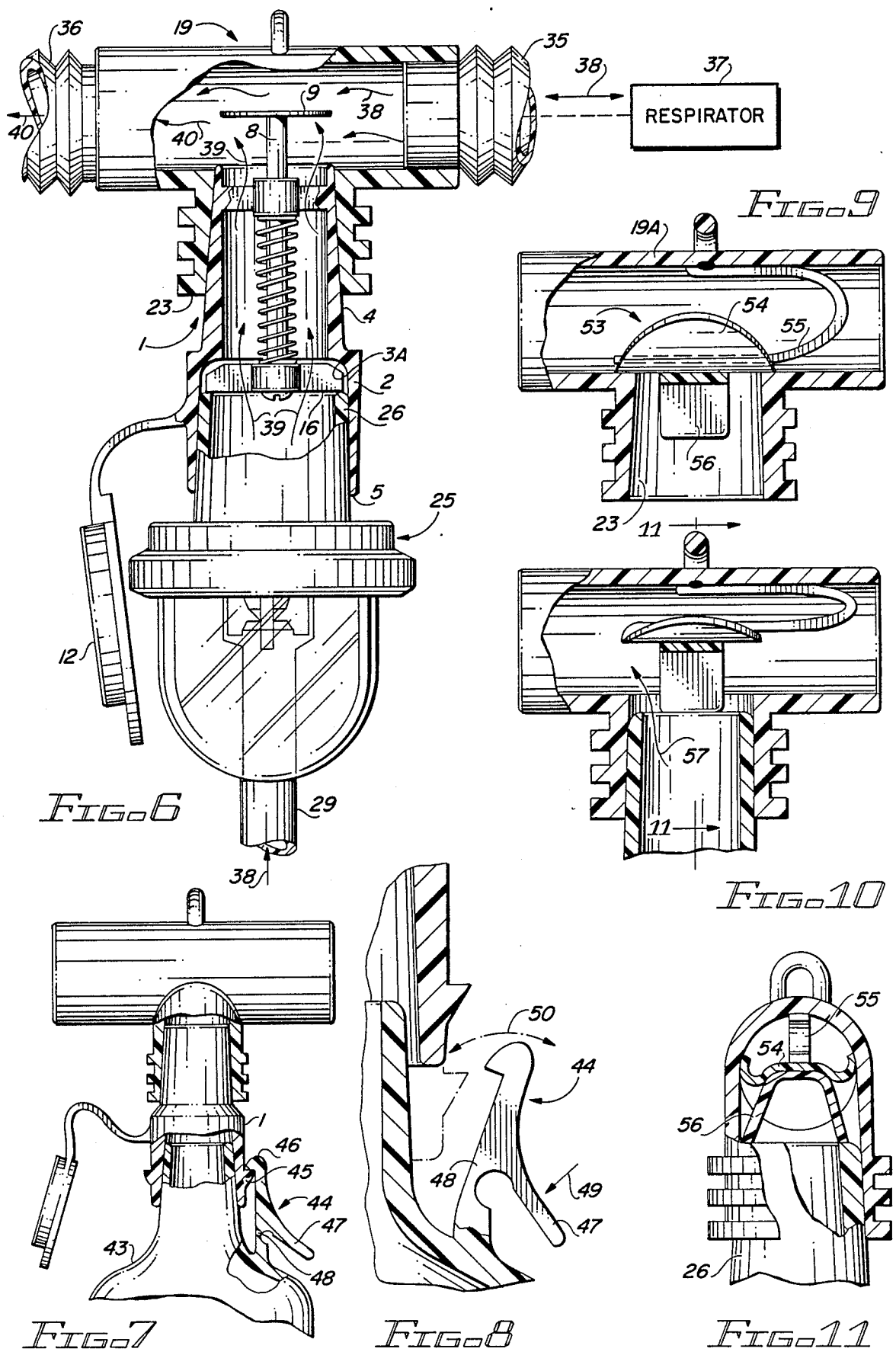

QUICK-CONNECT ADAPTER VALVE FOR CONNECTING NEBULIZER AND FLUID VENTILATOR HOSE

This is a continuation of application Ser. No. 204,014, filed June 8, 1988, now abandoned by David Thayer Sladek and entitled "QUICK-CONNECT ADAPTER VALVE FOR CONNECTING NEBULIZER AND FLUID VENTILATOR HOSE".

BACKGROUND OF THE INVENTION

The invention relates to ventilators, and particularly to a quick connect valve for connecting a nebulizer or a fluid collection reservoir into a hose of a respirator.

Patients having ventilatory difficulties often are connected to ventilators. A ventilator provides positive pressure in an inspirator hose, the opposite end of which is connected by means of a Y connector to a bronchial tube inserted into the patient's throat. An expiratory hose is connected to the remaining port of the Y connector, which is connected in series with an expiratory manifold that is closed so that air forced from the ventilator into the inspiratory hose forces a "breath" into the patient. When the expiratory manifold opens, reducing pressure in the bronchial tube, pressure in the patient's lungs allows exhalation through the expiratory manifold.

It is frequently necessary to apply a mist of liquid medication into the air stream forced through the inspiratory hose by the ventilator. In present practice, the inspiratory hose is disconnected from the ventilator, a T connector is used to reconnect the inspiratory hose to the ventilator, and a tapered female end of the nebulizer is inserted into the remaining port of the T connector. The liquid medication mist then is injected from the nebulizer into the inspiratory air stream. When the nebulizer is removed, the inspiratory hose again is disconnected, the T connector is removed, and inspiratory hose is reconnected to the ventilator.

There are a number of highly undesirable aspects to this previous technique for injecting medication mist from a nebulizer into the inspiratory hose. The disconnecting of certain patients from the positive pressure in the inspiratory hose can be dangerous, because maintaining a minimum level of positive pressure in the inspiratory hose may prevent partial collapsing of the lungs in certain patients. Mucous and condensation frequently build up on the inner walls of the inspiratory hose. Breaking the connection of the inspiratory hose to the ventilator exposes those hospital personnel to the mucous, which may leak out of the disconnected end of the hose, and hence to the bacteria therein. Opening the inspiratory hose also can allow microorganisms which are usually present in hospitals to enter into the inspiratory stream, providing a wide open path directly into the patient's lungs, possibly inducing infection which might be dangerous to the patient. Disconnecting the inspiratory hose may cause the bronchial tube to wobble in the patient's throat, causing considerable discomfort in some cases.

There clearly is a presently unmet need for an improved apparatus and method for injecting medicated mist from a nebulizer into the inspiratory air stream produced by a ventilator.

SUMMARY OF THE INVENTION

Accordingly, it is an object of the invention to provide an improved apparatus and technique for injecting medicated mist from a nebulizer into an inspiratory stream produced by a ventilator.

It is another object of the invention to provide an improved technique for draining accumulated fluids from the inspiratory hose of a ventilator.

It is another object of the invention to provide an improved method and apparatus for making fluid connection with the interior of a nebulizer hose without exposing it to airborne bacteria and the like.

It is another object of the invention to provide a method and apparatus that avoids exposure of hospital personnel to contamination from mucous and the like built-up in the inspiratory hose of a ventilator.

Briefly described, and in accordance with one embodiment thereof, the invention provides an inexpensive, disposable, plastic adaptor having a narrow neck that fits snugly into a lower inlet of a T connector permanently connected in the inspiratory stream of a ventilator, preferably close to a Y connector coupling the inspiratory hose and expiratory hose to a bronchial tube inserted in the throat of a patient. A widened body portion of the adaptor valve includes a spring loaded valve lifter mechanism that raises a planar valve plate above a planar lip around an upper mouth of the adapter valve, providing fluid communication between a nebulizer or drainage container that is inserted into the lower body of the adapter valve, thereby forcing the valve lifter mechanism upward and opening the valve. The adapter valve has a snap-on cap connected by a thin, flexible hinge to the body of the adapter valve. When the nebulizer or drain container is removed, the valve lifter mechanism is lowered, and the valve plate is lowered to cover the mouth of the adapter valve, sealing the interior of the ventilator. The snap-on cap then is pressed onto the open port of the T connector, preventing airborne bacteria and the like from contaminating the mouth of the adapter valve, and also preventing leakage of any mucous or the like from the interior of the inspiratory hose. The basic structure of the adapter valve includes a tubular housing, the valve plate, the valve lifting mechanism, which includes a vertical shaft journaled in a stationary hub, and three abutment members in the form of spokes connected to the lower end of the vertical shaft. When the tapered connection end of the nebulizer is forced into the lower cavity of the adapter valve, it pushes the abutment spokes upward, forcing the vertical shaft and valve plate upward, automatically opening the valve as the nebulizer is connected. In another utilization of the adapter valve, the tapered connection end of a drain container is inserted into the lower end of the adapter valve, raising the valve plate so that liquid in the inspiratory hose can drain into the reservoir.

BRIEF DESCRIPTION OF THE DRAWINGS

FIG. 1 is a perspective view of the adapter valve of the present invention.

FIG. 2 is a section view taken along section line 2—2 of FIG. 1.

FIG. 3 is a section view taken along section line 3—3 of FIG. 2.

FIG. 4 is a section view taken along section line 4—4 of FIG. 2.

FIG. 5 is an exploded perspective view illustrating use of the adapter valve of FIG. 1 to connect a nebulizer or a drain container in fluid connection with the interior of an inspiratory hose of a ventilator.

FIG. 6 is a partial cut-away elevation view illustrating connection of a nebulizer to a T connector in the inspiratory hose of a ventilator using the adapter valve of FIG. 1.

FIG. 7 is a partial cut-away elevation view illustrating use of the adapter valve of FIG. 1 to connect a fluid collection reservoir to a ventilator hose.

FIG. 8 is an enlarged partial section view illustrating a lock-on attachment of the fluid collection reservoir of FIG. 7.

FIG. 9 is a partial cut-away elevation view of an alternate embodiment of the invention.

FIG. 10 is a partial cut-away section view illustrating operation of the valve in FIG. 9.

FIG. 11 is a partial cut-away section view taken along section line 11—11 of FIG. 10.

DETAILED DESCRIPTION OF THE PREFERRED EMBODIMENTS

Referring to FIGS. 1-4, adapter valve 1 includes a lower cylindrical section 2 having an inlet 5. A tapered upper section 4 is attached to the upper end of lower section 2. A shoulder 3 is positioned between lower section 2 and upper section 4. A circular lip 6 surrounds the open upper end of section 4.

A movable, planar valve plate 9 is attached to the upper end of a shaft 8 which is journaled in a hub 10. Hub 10 is rigidly supported by 3 spokes 11 that are attached to the inner surface of upper section 4.

The diameter of valve plate 9 is the same as the outside diameter of circular lip 6, so that when the lower edge of valve plate 9 rests on lip 6, a good seal is formed between lip 6 and valve plate 9.

A snap-on cap 12 is connected by a flexible hinge strap 13, and snaps on to cover the inlet 5 of adapter valve 1. As shown in FIG. 2, cap 12 has a recess 12A into which the lower end of lower section 2 fits snugly.

As best seen in FIG. 2, the lower mouth 5 opens into a cylindrical cavity 14 having a rounded annular upper shoulder 3A. Cavity 14 opens into a cavity 15 of smaller diameter in upper section 4.

As also best seen in FIG. 2, the lower end of shaft 8 is attached to a hub 18 having 3 spokes 16 extending radially outwardly therefrom at equal angular intervals almost to the inner wall of cavity 14.

A compression coil spring 17 is disposed around vertical shaft 8 and is anchored against the lower edge of hub 10 and the upper edge of hub 18, thereby urging spokes 16, and hence shaft 8 and valve plate 9, downward so that adapter valve 1 is normally closed. The assembly including spokes 16 and vertical shaft 8 act as a valve lifter.

The adapter valve 1, including cap 12, can be composed of resin, polystyrene, ABS plastic, or any of many other plastic materials, except for spring 17 and a metal screw or solvent bonding material attaching hub 18 to the lower end of shaft 8.

Referring next to FIG. 5, the upper tapered section 4 of adapter valve 1 can be inserted into an opening 23 in a standard T connector 19 which. Ports 22 and 24 of T connector 19 engage ends of sections 35 and 36 of an inspiratory hose of a ventilator used to aid breathing of hospital patients. A loop 20 on top of T adapter 19 facilitates supporting the ventilator hose in a convenient fashion.

To effectuate convenient attachment of a nebulizer 25 to T connector 19, the adapter valve 1 is first inserted into port 23 of T connector 19. Valve plate 9 remains closed. Then, as best shown in FIG. 6, the tapered upper end 26 of nebulizer 25 is inserted through opening 5 into recess 14. The upper edges of section 26 of the nebulizer 25 engage the lower surfaces of spokes 16, pushing shaft 8 and valve plate 9 upward, as indicated in FIG. 6. Pressurized air 38 connected to the inlet 29 of nebulizer 25 produces a mist of liquid medication contained in the bowl of an ordinary nebulizer 25 by venturi action. The mist flows upward, as indicated by arrows 39, through the open upper end of adapter valve 1 and is injected into the pressurized air stream in inspiratory hose 35, 36. Reference numeral 38 designates the direction of air flow pumped by ventilator 37.

When all of the liquid medication dose in nebulizer 25 has been injected into the inspiratory air stream produced by ventilator 37, nebulizer 25 is pulled downward out of the lower section 2 adapter valve 1. However, adapter valve 1 remains in place in T connector 19, so valve plate 9 is closed, preventing any of the air stream 38 from escaping, and also preventing any mucous or condensate build-up inside inspiratory hose 35, 36 from draining out of port 23 of T connector 19. Cap 12 then is pressed onto the lower opening to cover the lower opening 5 of adapter valve 1 preventing any infection-producing bacteria from building up on the inside surfaces of adapter valve 1.

The above described adapter valve structure can be used to very conveniently administer a dose of medication mist to the patient whenever desired, without temporarily disrupting the "positive end expiratory pressure" (PEEP) which is necessary in some patients. Also, a trap or reservoir such as 30 in FIG. 5 having a tapered connection end 31 with a passage 32 therethrough can be inserted through the inlet end 5 of adapter valve 1 to allow liquid, mucous, etc., that may build up within inspiratory hose 35, 36 and T connector 19 to drain into the container, which then can be conveniently disposed of.

FIG. 7 shows a slight modification to adapter valve 1 wherein a locking flange 45 is provided around the periphery of lower section 2. A drain reservoir 43 having an upper nozzle and insertable through opening 5 of adapter valve 1 has a latch 44 connected by a hinge strap 48 to the drain reservoir A hook end 46 snaps over locking flange 45 in the manner shown in FIGS. 7 and 8. Depressing a handle 47 pivots the locking hood 45 in the direction indicated by arrow 50 in FIG. 8 to release the latch 44. The advantage of this structure is that it prevents the weight of fluid accumulated in drain reservoir 43 from causing the connecting end to be pulled out of the lower end of adapter valve 1. Preferably, solvent bonding material is used to secure adapter valve 1 in port 23 of T connector 19.

FIGS. 9-11 show an alternate embodiment of the invention, wherein a valve 53 is disposed inside T connector 19A. Valve 53 includes a flexible valve membrane 54 which covers the opening from the interior of the main channel of the T connector 19A into its lower port 23. This valve is normally closed. A bias spring 55 presses the center portion of membrane 53 tightly against the opening between port 23 and the main horizontal channel of T connector 19A.

A U-shaped member 56 is attached to the bottom of membrane 54. The lower ends of U-shaped member 56 extend downward into port 23, and are engaged by the upper tapered section 26 of a nebulizer when it is inserted into port 23, as shown in FIG. 11, lifting the center portion of membrane 54 up. Mist from the nebulizer then can flow through port 23 and be injected into the main channel of T connector 19A, as shown in FIG. 10.

The above described device provides a number of advantages over the prior technique of disconnecting the inspiratory hose to connect a nebulizer or drain reservoir thereto. The T connector 19 can be permanently inserted in the inspiratory hose line, preferably close to the Y connector, so that injected mist does not have time to condense out or become deposited on the inner walls of the inspiratory hose. The PEEP pressure is maintained, which is a major advantage for certain patients. Unsanitary leakage of mucous within the inspiratory hose is avoided A similar T connector such as 19 and adapter valve such as 1 can be inserted into the expiratory hose of the ventilatory system for the purpose of conveniently attaching drain bags to it, if necessary. When no nebulizer or drain reservoir is attached to the adapter valve 1, the press-on cap 12 allows the interior to be safely sealed, preventing contamination by airborne bacteria, etc., which are frequently a problem in hospitals. The cap 12 can be kept on the lower end of the adapter valve 1 during storage and shipment, again maintaining a sanitary interior of the adapter valve.

While the invention has been described with reference to several particular embodiments thereof, those skilled in the art will be able to make various modifications to the invention without departing from the true spirit and scope thereof. For example, the adapter valve 1 can be permanently integrally incorporated as a part of the T connector 19.

What is claimed is:

1. An adapter/valve device for quick-connect coupling or decoupling of an accessory such as a nebulizer or a drain container to a three port coupler of a ventilator hose without interrupting positive pressure of gas in the ventilator hose or exposing the interior of the ventilator hose to outside contamination, the adapter valve comprising in combination:
   (a) a generally tubular housing with a tapered upper end adapted for insertion into a port of the three port coupler, the housing including
      i. a generally cylindrical lower cavity adapted to receive insertion of an open-ended tubular connector of the accessory,
      ii. a generally cylindrical upper cavity coaxial with the lower cavity, the lower cavity and upper cavity forming a passage through the housing, an upper end of the housing forming a planar, circular lip which is approximately flush with a wall of a passage of the ventilator hose extending through the three port coupler;
   (b) a stationary hub centered in the upper cavity adjacent to the lip and a plurality of spaced spokes attaching the stationary hub to a wall of the upper cavity;
   (c) a valve assembly including
      i. a planar circular disc forming a valve plate,
      ii. a rod perpendicular to the disc and passing through a hole in the stationary hub and having an upper end rigidly attached to the disc,
      iii. a compression spring disposed around the rod and having an upper end abutting the stationary hub,
      iv. a movable hub located in the lower cavity and rigidly attached to a lower end of the rod, a lower end of the spring abutting the movable hub, urging the disc against the lip to form a seal therewith, and a plurality of spaced abutment spokes each having an inner end rigidly attached to the movable hub and an outer end adjacent to and spaced from a wall of the lower cavity, the abutment spokes being adapted to abut a circular wall end of the tubular connector as it is inserted into the lower cavity and thereby raise the disc away from the lip, exposing an interior of the ventilator tube and the three port coupler to an interior of the accessory, the valve assembly resealing the disc with the lip when the tubular connector is withdrawn from the first cavity.

2. The adapter/valve device of claim 1 wherein the housing, stationary hub, disc, rod, movable hub, spokes of the stationary hub, and abutment spokes are plastic.

3. The adapter/valve device of claim 2 wherein a diameter of the lower cavity is greater than a diameter of the upper cavity, there being a shoulder between the upper cavity and the lower cavity, the outer ends of the abutment spokes abutting the shoulder to limit upward movement of the disc.

4. The adapter/valve device of claim 3 including a removable plastic cap fitting snugly over a bottom end of the housing and a plastic hinge connecting the cap to the housing.

5. A method of introducing medication mist into a ventilator hose via a three port coupler having first and second ports connected into the ventilator hose, without interrupting positive pressure of gas in the ventilator hose, the method comprising the steps of:
   (a) providing an adapter/valve having a plurality of abutment spokes at a first end
   (b) inserting a tapered end of the adapter/valve device in a third port of the three port coupler;
   (c) inserting an end of a tubular connector of a nebulizer into a cavity of the adapter/valve device;
   (d) abutting the plurality of abutment spokes attached to the first end of a valve lifter rod to open a valve assembly including a planar disc attached to a second end of the valve lifter rod, a planar lip surrounding a passage extending through the adapter/valve device and the tubular connector of the nebulizer, whereby gas flowing through the ventilator hose and the first and second ports of the three port coupler creates Venturi suction that draws medication mist out of the nebulizer through the passage, through a gap between the planar lip and the disc, and into the ventilator hose, whereby positive pressure of gas in the nebulizer hose is not interrupted during the connection of the nebulizer to the adapter/valve device;
   (e) removing the nebulizer from the adapter/valve
   (f) closing the valve by urging the disc against the planar lip by means of the valve rod as the end of the tubular connector is withdrawn, without interrupting the positive pressure of the gas in the ventilator tube.

* * * * *